United States Patent
Chornenky et al.

(10) Patent No.: US 6,377,846 B1
(45) Date of Patent: *Apr. 23, 2002

(54) DEVICE FOR DELIVERING LOCALIZED X-RAY RADIATION AND METHOD OF MANUFACTURE

(75) Inventors: Victor I. Chornenky, Minnetonka; Michael R. Forman, St. Paul, both of MN (US)

(73) Assignee: Medtronic AVE, Inc., Santa Rose, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/806,244

(22) Filed: Feb. 21, 1997

(51) Int. Cl.[7] .............................. A61N 1/30; A61B 18/18
(52) U.S. Cl. .............................. 604/20; 607/92; 606/14
(58) Field of Search .............................. 604/20, 21, 22, 604/113, 114; 607/88–94; 606/2, 3, 7, 13, 14

(56) References Cited

U.S. PATENT DOCUMENTS

| | | |
|---|---|---|
| 1,786,373 A | 12/1930 | Walker |
| 1,881,448 A | 10/1932 | Forde et al. |
| 2,173,258 A | 9/1939 | Lederer |
| 2,467,812 A | 4/1949 | Clapp |
| 2,766,385 A | 10/1956 | Herrnring et al. |
| 3,005,096 A | 10/1961 | Chynoweth |
| 3,073,960 A | 1/1963 | Guentner et al. |
| 3,125,679 A | 3/1964 | Ohde et al. |
| 3,256,439 A | 6/1966 | Dyke et al. |
| 3,348,051 A | 10/1967 | Weighart et al. |
| 3,381,129 A | 4/1968 | Duftschmid |
| 3,388,314 A | 6/1968 | Gould |
| 3,484,721 A | 12/1969 | Bond et al. |
| 3,508,059 A | 4/1970 | Vanderpool |
| 3,538,919 A | 11/1970 | Meyer |
| 3,564,251 A | 2/1971 | Youmans |
| 3,582,702 A | 6/1971 | Almer |
| 3,617,939 A | 11/1971 | Bond et al. |
| 3,628,021 A | 12/1971 | MacDonald |
| 3,691,417 A | 9/1972 | Gralenski |
| 3,714,486 A | 1/1973 | Mccrary |

(List continued on next page.)

FOREIGN PATENT DOCUMENTS

| | | |
|---|---|---|
| DE | 2054738 | 5/1972 |
| DE | 26 08 418 | 9/1977 |
| EP | 0 359 724 | 3/1990 |
| EP | 0 572 170 A1 | 12/1993 |

(List continued on next page.)

OTHER PUBLICATIONS

Borghi, Dr. M., "St 121 and ST 122 Porous Coating Getters", *SAES Getters S.p.A.*, pp. 1–13 (Jul. 27, 1994).

Brandes, George R., "Diamond Vacuum Electronics", *Advanced Technology Materials, Inc.*, Chapter 17, pp. 1–27.

Choi, W. B., et al., "Field emission from diamond coated molybdenum filed emitters", *American Vacuum Society, J. Vac. Sci. Technol.*, B 14(3), pp. 2050–2055 (May/Jun. 1996).

(List continued on next page.)

*Primary Examiner*—Sharon Kennedy

(57) ABSTRACT

Generally, the present invention provides a device for insertion into a body of a subject being treated to deliver localized x-ray radiation, and a method for fabricating such a device. The device includes a cathode structure that has a thin, diamond film as a cathode. The device further comprises a vacuum housing and an anode. A method for fabricating a device for localized x-ray radiation is described which includes the formation of a thin diamond film on a getter at temperatures below an activation temperature of the getter.

13 Claims, 2 Drawing Sheets

U.S. PATENT DOCUMENTS

| | | |
|---|---|---|
| 3,752,990 A | 8/1973 | Fischer |
| 3,866,050 A | 2/1975 | Whitfield |
| 3,878,394 A | 4/1975 | Golden |
| 3,883,760 A | 5/1975 | Cunningham, Jr. |
| 3,920,999 A | 11/1975 | Drexler et al. |
| 3,970,884 A | 7/1976 | Golden |
| 3,987,281 A | 10/1976 | Hodes |
| 4,058,486 A | 11/1977 | Mallozzi et al. |
| 4,060,731 A | 11/1977 | Rissi |
| 4,097,759 A | 6/1978 | Furbee et al. |
| 4,104,526 A | 8/1978 | Albert |
| 4,104,530 A | 8/1978 | Weiss |
| 4,104,531 A | 8/1978 | Weiss |
| 4,104,532 A | 8/1978 | Weiss |
| 4,109,154 A | 8/1978 | Taumann |
| 4,117,334 A | 9/1978 | Strauts |
| 4,143,275 A | 3/1979 | Mallozzi et al. |
| 4,158,138 A | 6/1979 | Hellstrom |
| 4,163,901 A | 8/1979 | Azam et al. |
| 4,164,680 A | 8/1979 | Villalobos |
| 4,191,193 A | 3/1980 | Seo |
| 4,344,181 A | 8/1982 | Baecklund |
| 4,359,660 A | 11/1982 | Smith et al. |
| 4,368,538 A | 1/1983 | Mccorkle |
| 4,563,769 A | 1/1986 | Madsen |
| 4,607,380 A | 8/1986 | Oliver |
| 4,636,195 A | 1/1987 | Wolinksy |
| 4,646,338 A | 2/1987 | Skillicorn |
| 4,669,467 A | 6/1987 | Willett et al. |
| 4,670,894 A | 6/1987 | Birnbach et al. |
| 4,694,480 A | 9/1987 | Skillicorn |
| 4,701,941 A | 10/1987 | Szirmai et al. |
| 4,702,228 A | 10/1987 | Russell, Jr. et al. |
| 4,715,054 A | 12/1987 | Kato et al. |
| 4,763,671 A | 8/1988 | Goffinet |
| 4,789,997 A | 12/1988 | Madsen et al. |
| 4,794,931 A | 1/1989 | Yock |
| 4,800,581 A | 1/1989 | Kujirai et al. |
| 4,824,436 A | 4/1989 | Wolinsky |
| 4,856,036 A | 8/1989 | Malcolm et al. |
| 4,913,142 A | 4/1990 | Kittrell et al. |
| 4,924,485 A | 5/1990 | Hoeberling |
| 4,966,596 A | 10/1990 | Kuntz et al. |
| 4,976,266 A | 12/1990 | Huffman et al. |
| 4,979,199 A | 12/1990 | Cueman et al. |
| 4,987,007 A | 1/1991 | Wagal et al. |
| 5,042,486 A | 8/1991 | Pfeiler et al. |
| 5,059,166 A | 10/1991 | Fischell et al. |
| 5,077,771 A | 12/1991 | Skillicorn et al. |
| 5,087,244 A | 2/1992 | Wolinsky et al. |
| 5,090,043 A | 2/1992 | Parker et al. |
| 5,098,737 A | 3/1992 | Collins et al. |
| 5,099,845 A | 3/1992 | Besz et al. |
| 5,101,422 A | 3/1992 | Thiel et al. |
| 5,106,360 A | 4/1992 | Ishiwara et al. |
| 5,148,463 A | 9/1992 | Woodruff et al. |
| 5,153,900 A | 10/1992 | Nomikos et al. |
| 5,165,093 A | 11/1992 | Miller et al. |
| 5,199,939 A | 4/1993 | Dake et al. |
| 5,222,116 A | 6/1993 | Eloff et al. |
| 5,228,176 A | 7/1993 | Bui et al. |
| RE34,421 E | 10/1993 | Parker et al. |
| 5,264,801 A | 11/1993 | Decou, Jr. et al. |
| 5,290,275 A | 3/1994 | Kittrell et al. |
| 5,313,949 A | 5/1994 | Yock |
| 5,313,950 A | 5/1994 | Ishikawa et al. |
| 5,364,336 A | 11/1994 | Carr |
| 5,369,679 A | 11/1994 | Sliski et al. |
| 5,402,790 A | 4/1995 | Jang et al. |
| 5,414,748 A | 5/1995 | Upadhya |
| 5,422,926 A | 6/1995 | Smith et al. |
| 5,425,735 A | 6/1995 | Rosen et al. |
| 5,428,658 A * | 6/1995 | Gettinger et al. ........... 378/119 |
| 5,437,277 A | 8/1995 | Dumoulin et al. |
| 5,442,254 A | 8/1995 | Thomson |
| 5,442,678 A * | 8/1995 | Dinsmore et al. .......... 378/137 |
| 5,452,720 A | 9/1995 | Smith et al. |
| 5,453,575 A | 9/1995 | O'Donnell et al. |
| 5,454,809 A | 10/1995 | Janssen |
| 5,465,732 A | 11/1995 | Abele |
| 5,469,490 A | 11/1995 | Golden et al. |
| 5,474,075 A | 12/1995 | Goldberg et al. |
| 5,503,613 A | 4/1996 | Weinberger |
| 5,504,799 A | 4/1996 | Suzuki |
| 5,511,107 A | 4/1996 | Sliski |
| 5,528,652 A * | 6/1996 | Smith et al. .................. 378/65 |
| 5,566,221 A | 10/1996 | Smith et al. |
| 5,621,780 A | 4/1997 | Smith et al. |
| 5,623,139 A | 4/1997 | Sliski |
| 5,627,870 A * | 5/1997 | Wang ......................... 378/121 |
| 5,635,709 A | 6/1997 | Sliski et al. |
| 5,729,583 A | 3/1998 | Tang et al. |

FOREIGN PATENT DOCUMENTS

| | | |
|---|---|---|
| EP | 0 697 712 A1 | 2/1996 |
| EP | 0 718 864 A1 | 6/1996 |
| EP | 0 860 180 A2 | 8/1998 |
| EP | 0 860 181 A2 | 8/1998 |
| FR | 2 672 734 | 8/1992 |
| GB | 230183 | 3/1925 |
| GB | 997352 | 7/1965 |
| JP | 58-145098 A | 8/1983 |
| JP | 08-153460 | 6/1996 |
| RU | 814331 | 3/1981 |
| WO | WO 95/20241 | 7/1995 |
| WO | WO 96/02059 | 1/1996 |
| WO | WO 97/06549 | 2/1997 |
| WO | WO 97/07740 | 3/1997 |

OTHER PUBLICATIONS

Davanloo, F., et al., "Amorphic diamond films produced by a laser plasma source", *American Institute of Physics, J. Appl. Phys.*, 67(4), pp. 2081–2087 (Feb. 15, 1990).

Geis, M. W., et al., "Diamond emitters fabrication and theory", *American Vacuum Society, J. Vac. Sci. Technol.*, B 14(3), pp. 2060–2067 (May/Jun. 1996).

Giorgi, E., et al., "High Porosity Thick Film Gettters", *SAES Getters S.p.A.*, pp. 1–20.

Giorgi, T.A., "Getters and Gettering", *Japan J. Appl. Phys. Suppl. 2, Pt. 1*, pp. 53–60 (1974).

Giorgi, T.A., et al., "An updated review of getters and gettering", *American Vaccum Society, J. Vac. Sci. Technol.*, A 3(2), pp. 417–423 (Mar./Apr. 1985).

Givargizov, E.I., et al., "Growth of diamond particles on sharpened silicon tips", *Elsevier Science Publishers B.V., Materials Letters* 18, pp. 61–63 (1993).

Givargizov, E. I., "Silicon tips with diamond particles on them: New filed emitters?", *American Vacuum Society, J. Vac. Sci. Technol.*, B 13(2), pp. 414–417 (Mar./Apr. 1995).

Himpsel, F. J., et al., "Quantum photoyield of diamond (111) —A stable negative–affinity emitter", *The American Physical Society, Physical Review B*, vol. 20, No. 2, pp. 624–627 (Jul. 15, 1979).

Kitahama, K., et al., "Synthesis of diamond by laser–induced chemical vapor deposition", *American Institute of Physics, Appl. Phys. Lett.*, 49 (11), pp. 634–635 (Sep. 15, 1996).

Kumar, N., et al., "Diamond–based field emission flat panel displays", *Solid State Technology*, pp. 71–73 (May 1995).

Liu, J. et al., "Field emission charcteristics of diamond coated silicon field emitters", *American Vacuum Society, J. Vac. Sci. Technol.*, B 13(2), pp. 422–426 (Mar./Apr. 1995).

Okano, K., et al., "Electron emission from phosphorous and boron–doped polycrystalline diamond films", *Electronic Letters*, vol. 31, No. 1, pp. 74–75 (Jan. 5, 1995).

Porta, Dr. P. d., ""Gettering" an Integral Part of Vacuum Technology", American Vacuum Society 39th National Symposium, Technical Paper 202, pp. 1–15 (Nov. 9–13, 1992).

Sato, T., et al., "Deposition of Diamond–like Carbon Films by Pulsed–Laser Evaporation", *Japanese Journal of Applied Physics*, vol. 26, No. 9, pp. 1487–1488 (Sep. 1987).

Zhirnov, V. V., et al., "Emission stability and high current performance of diamond–coated Si emitters", *American Vacuum Society, J. Vac. Sci. Technol.*, B 14(3), pp. 2034–2036 (May/Jun. 1996).

Wang, C., et al., "Cold Field Emission From CVD Diamond Films Observed in Emission Electron Microscopy", *Electronics Letters*, vol. 27, No. 16, pp. 1459–1461 (Aug. 1, 1991).

Gundel, et al., *Nuclear Instruments and Methods in Physics Research*, A280:1–6 (1989).

Gundel, et al., *J. Appl. Phys.*, 69:(2):975–982 (Jan. 1991).

Hehrlein, et al., *Circulation*, 92(6):1570–1575 (Sep. 1995).

March, et al., *Circulation*, 87(1):184–191 (Jan. 1993).

Matsuda, et al., *Journal of Materials Science*, 21:649–658 (1986).

Matsuda, et al., *Densitny and deposition rate of chemical –vapour–deposited boron nitride, Journal of Materials Science*, 23:509–514 (1988).

Papillon, *Diseases of the Colon& Rectum*, 27(11):695–700 (Nov. 1984).

Phillips, *Radiology*, 90(3):525–531 (Mar. 1968).

Pouch, et al., *Materials Science Forum*, 54&55:141–152 (1990).

Riege, *Nucl. Inst. and Meth. in Phys. Res.*, A340:80–89 (1994).

Schwartz, et al., *JACC*, 19(5):1106–1113 (Apr. 1992).

Soares, et al., *Nuclear Technology Publishing*, 47(174):367–372 (1993).

Strickland, *Clinical Radiology—The J. of the Faculty of Radiologists*, XVI(1–4):112–118 (Jan. to Oct. 1965).

Sugiyama et al., *Chemical Vapor Deposition of Turbostratic and Hexagonal Boron Nitride*, Mateials Science Forum, 54 & 55:141–152 (1990).

Verin, et al., *Circulation*, 92:(8):2284–2290 (Oct. 1995).

Waksman, et al., *Circulation*, 92(6):1383–1386 (Sep. 1995).

Waksman, et al., *Circulation*, 92(10):3025–3031 (Nov. 1995).

Waksman, et al., *Circulation*, 91(5):1533–1539 (Mar. 1995).

Wang, et al., *Int. J. Radiation Oncology Biol. Phys.*, 9 (8):1185–1189 (Aug. 1983).

Wiedermann, et al., *JACC*, 23(6):1491–1498 (May 1994).

Wiedermann, et al., *JACC*, 25(6):1451–1456 (May 1995).

Wiedermann, et al., "Effects of high–dose intracoronary irradiation on vasomotor function and smooth muscle histopathology", pp. H125–H132 (1994).

Asano, et al., *Jp. J. Appl. Phys.*, 31(Part 1, 9B):3098–3101 (Sep. 1992).

Brady, et al., *Gynecologic Oncology*, 2:314–323 (1974).

Brochure: "Dunlee DL–1 Stationary Anode Insert", Dunlee Corporation, Bellwood, IL 60104, Jun. 1972.

Condado, et al., 1 page, *Discoveries in Radiation for Restenosis*, Emory University School of Medicine (Jan. 1996).

Fischell, et al., *Circulation*, 90(6): 2956–2963 (Dec. 1994).

Geissler, et al., *Physics Letters A*, 176:387–392 (1993).

* cited by examiner

DEVICE FOR DELIVERING LOCALIZED X-RAY RADIATION AND METHOD OF MANUFACTURE

I. FIELD OF THE INVENTION

The present invention is directed to an x-ray device and method of fabrication, and more particularly to an x-ray device and method for fabrication for delivering localized radiation to vessels, lumens, or cavities of a body, such as cardiovascular tissue, to treat restenosis and other conditions.

II. BACKGROUND OF THE INVENTION

In the medical field, doctors and scientists strive to find less invasive ways to treat patients. By using treatments that are less intrusive to the body, doctors can greatly reduce the stress on the patient's systems and exposure to infection. For example, laparoscopic techniques enable physicians to explore the interior of the body and perform surgery through a small opening in the skin. Less intrusive medical techniques are extremely beneficial when applied to cardiovascular diseases.

Cardiovascular diseases affect millions of people, often causing heart attacks and death. One common aspect of many cardiovascular diseases is stenosis, or the thickening of the artery or vein, decreasing blood flow through the vessel. Angioplasty procedures have been developed to reopen clogged arteries without resorting to a bypass operation. However, in a large percentage of cases, arteries become occluded again after an angioplasty procedure. This recurrent thickening of the vessel is termed restenosis. Restenosis frequently requires a second angioplasty and eventual bypass surgery. Bypass surgery is very stressful on the patient, requiring the chest to be opened, and presents risks from infection, anesthesia, and heart failure.

Effective methods of preventing or treating restenosis could benefit millions of people. One approach uses drug therapy to prevent or minimize restenosis. For example, Heparin has been used as an anticoagulant and an inhibitor of arterial smooth muscle proliferation. Dexamethasone is another drug which may prevent smooth muscle proliferation. It has been suggested that such anticoagulants and antiproliferative agents may be effective at preventing restenosis after an angioplasty procedure thereby eliminating the necessity to repeat the procedure.

To be most effective and to reduce the associated risk, it is desirable to deliver such drugs directly to the region to be treated. In order to minimize the invasiveness of the procedure a drug delivery device that is adapted to traverse the human cardiovascular or circulatory system must be used. Such a device must be capable of entering small blood vessels with diameters of about two to four millimeters. Such a device must also be capable of making hairpin turns as it follows a tortuous path.

Many types of catheters have therefore been developed to deliver these and other effective drugs to the site of the restenosis. These catheters frequently use pressure to drive the drug into the tissue or plaque, potentially causing damage to the lumen wall. Techniques of delivery which do not use pressure use occlusion balloons to isolate the area from blood flow to enable sufficient absorption of the medication. However, the blood flow in an artery can only be occluded for a limited period of time while the drug is delivered. Due to these and other problems, localized delivery of drugs has not provided adequate treatment to prevent or reduce restenosis.

Another treatment for restenosis that has been attempted is beta-irradiation of the vessel wall by positioning radioactive isotopes in the vessel at the site of the restenosis. However, the depth of the penetration of the radiation is impossible to control with this method. The depth of the radiation is determined by the type of the radio-isotope used. The radioactive source will also irradiate other healthy parts of the body as it is brought to the site to be treated. Another disadvantage is that medical personnel must take extensive precautions when handling the radioactive material.

Thus, there is a need for effective methods and devices to treat the interior of the body with minimal intrusion. Effective, less invasive techniques for preventing and treating stenosis and restenosis at a lumen wall are especially needed.

III. SUMMARY OF THE INVENTION

Generally, the present invention provides a device to deliver localized x-ray radiation, and a method for fabricating such a device. In one particular embodiment of the invention, the device includes a cathode structure that has a thin, diamond film. The device further comprises an anode disposed within the vacuum housing, the diamond film being operative with the anode to produce localized x-ray radiation. In alternate embodiments, the device may further include a connector or a shaft, connected to the vacuum housing.

In another particular embodiment of the invention, a device to deliver localized x-ray radiation includes a cathode structure comprising a thin, diamond film on a getter. This device further comprises an anode disposed within a vacuum housing, the diamond film being operative with the anode to generate localized radiation.

In another particular embodiment of the invention, a method for fabricating a device for localized x-ray radiation is described which includes the formation of a thin diamond film on a shaped getter using a laser ion source. The method includes the steps of providing a getter with a shaped surface, where the getter has an activation temperature, and forming a thin diamond film cathode on the getter at temperatures below the activation temperature. The method further comprises disposing the cathode in a vacuum housing and increasing the temperature to the activation temperature of the getter.

In another particular embodiment of the invention, a transmissive device for insertion into the body of a patient is disclosed including a catheter and a flexible coaxial cable that is capable of conducting a voltage of greater than or equal to 10 kilovolts without electrical discharge.

In another particular embodiment of the invention, a method for conducting current in a body is disclosed, using the transmissive device of this invention.

In another particular embodiment of this invention, a device for insertion into a body includes a connector and a composite structure of boron nitride that joins a cathode and an anode.

IV. BRIEF DESCRIPTION OF THE DRAWINGS

The invention may be more completely understood in consideration of the detailed description of various embodiments of the invention which follows in connection with the accompanying drawings, in which.

Figure 1:
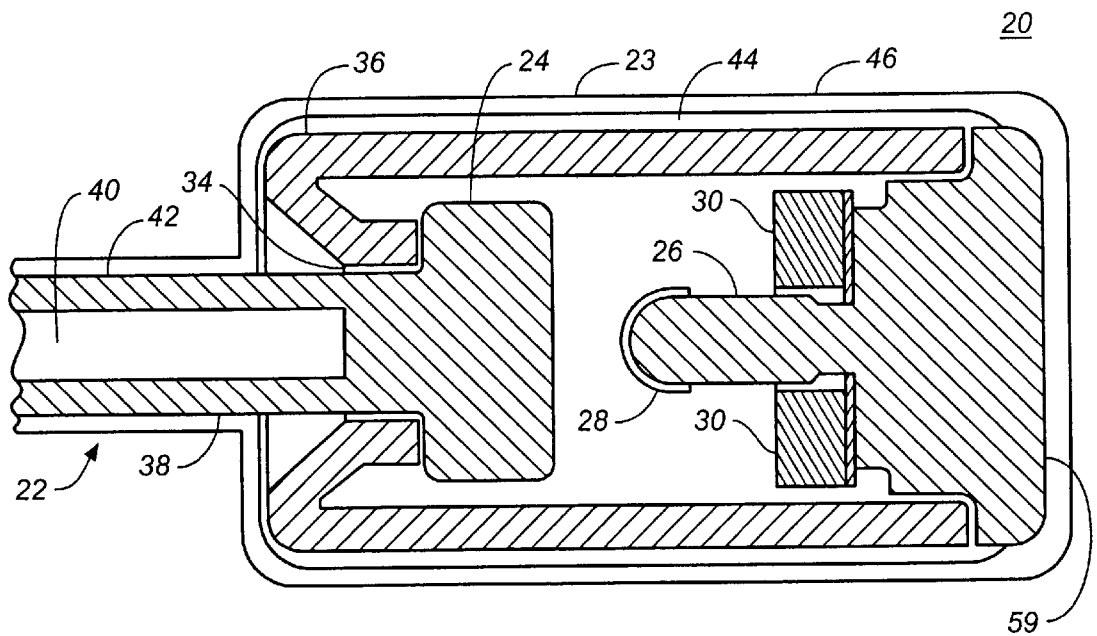
FIG. 1 shows an exploded cross-sectional view of an embodiment of the x-ray device of the present invention.

While the invention is amenable to various modifications and alternative forms, specifics thereof have been shown by way of example in the drawings and will be described in detail. It should be understood, however, that the intention is not to limit the invention to the particular embodiments described. On the contrary, the invention is to cover all modifications, equivalents, and alternatives falling within the spirit and scope of the invention as defined by the appended claims.

V. DETAILED DESCRIPTION OF THE VARIOUS EMBODIMENTS

The present invention is applicable to a variety of devices, methods of fabrication, methods of use, systems and arrangements which irradiate lumens, vessels, or interior sites in a body with x-ray radiation. The invention is particularly advantageous in preventing restenosis in the cardiovascular system. While the present invention is not so limited, an appreciation of various aspects of the invention is best gained through a discussion of application examples operating in such an environment.

FIG. 1 illustrates a first embodiment in which a cathode of an x-ray device 20 comprises a thin diamond film 28 which may be used to deliver localized x-ray radiation to treat, for example, restenosis. In coronary applications, it is desirable to have the x-ray radiation penetrate into the adventitia tissue of the blood-vessel about 2 millimeters deep. Penetration into the cardiac muscle tissue should be minimized. It is further desirable to deliver x-ray radiation with a peak energy of about 8–10 kiloelectronvolts (keV) in coronary applications.

While attempting to produce x-ray radiation of about 8–10 keV in the body, it is important to keep the magnitude of the electrical field at the surface of the cathode as low as possible. An electrical field exists at the surface of the cathode 26, while just on the outside of the vacuum housing a conductive braid or solder 44 is held at ground. An electrical discharge from the surface of the cathode to ground, or an electric flashover, must be prevented. According to the present invention, as a weaker electrical field is required by the x-ray source, the danger of electrical flashover is reduced, less heat is generated, and a wider array of conductors can be used.

In addition, the ability to lower the required electric field at the cathode results in a less expensive manufacturing technique. Small irregularities on the surface of the cathode result in an increase in the magnitude of the electrical field for an applied voltage, thereby increasing the chance of electrical flashover. The weaker the required electrical field at the cathode, the more imperfections can be tolerated on the cathode surface without risking flashover.

In accordance with one embodiment of the invention x-ray radiation is produced, while keeping the required electrical field low, by using a diamond film as a cathode. Diamond coatings display attractive properties as field emitters, losing electrons easily as a field is applied. Where a diamond coating is used as the cathode, the electrical field required to produce about 8–10 keV of radiation is about 20 keV/micron. In contrast, the required electrical field to produce a similar level of radiation from a metal emitter is well over 1,000 keV/micron. In the present invention, a diamond-coated cathode is used to achieve x-ray treatment radiation while producing significantly weaker electrical fields at the cathode.

X-ray devices for use inside a body are discussed in co-pending U.S. application Ser. No. 08/701,764, filed Aug. 24, 1996, the entire contents of which are incorporated herein by reference.

Now referring to FIG. 1, in this embodiment, the x-ray device 20, or transmission comprises a flexible catheter shaft 22 adapted for insertion into blood vessels, lumens, or other body cavities. While in this particular embodiment a catheter shaft is shown, generally, many different elements could be used to guide the x-ray device of the present invention to a treatment site. The shaft 22 has a proximal and distal portion, the distal portion being shown in FIG. 1. In coronary applications, the device may be inserted in the body at the femoral artery and threaded through a network of blood vessels to reach the heart. In this context the shaft must be extremely flexible and have a maximum diameter less than or equal to about 3 millimeters. In other applications, the properties of the shaft must meet the requirements of the task.

At the distal portion of the flexible shaft 22, a composite structure is coupled. The composite structure includes a vacuum housing 23 that encloses the x-ray source components. The x-ray source components include an anode 24, a cathode base 26, a thin diamond film 28 located on the cathode base 26, and a getter 30. The outer diameter of the integrated x-ray device shown in FIG. 1 is less than or equal to approximately 2.5 millimeters.

In order to apply an electric field across the anode and cathode, conductor or a coaxial cable 38 may be disposed within the shaft 22. In this embodiment, the coaxial cable 38 is coupled to a high voltage generator, not shown, at the proximal end of the shaft 22. An internal conductor 40 of the coaxial cable 38 is coupled to the anode 24 at the appropriate voltage. An external conductive layer 42 of the coaxial cable 38 is held at ground and coupled to the cathode base 26 via a conductive solder 44. Other known methods may also be used to apply the electric field across the anode and cathode.

A coronary artery after dilatation by angioplasty typically has a diameter of only about 3.0 millimeters. Therefore, a coaxial cable and any covering used in this device must have a diameter of less than or equal to 3.0 millimeter. The cable must also be able to carry the required voltages and have sufficient flexibility to make numerous sharp turns as it follows the artery path. Standard high voltage coaxial cables are generally not flexible enough. However, the inventors have found that miniature high frequency coaxial cables with an outer diameter of approximately 1.0 millimeter to 3.0 millimeters are available which also exhibit sufficient flexibility. These types of cables are typically used in high frequency applications at voltages less than several kilovolts (kV). In connection with the present invention, the inventors have discovered that such cables can hold direct current voltages as high as 75–100 kV without breakdown. Therefore, these cables are well suited for use with the x-ray device of the present invention. In one embodiment, a cable with an outer diameter less than or equal to 3.0 millimeters is used. In another embodiment, the cable has an outer diameter of 1–2 millimeters. Such cables are manufactured by, for example, New England Electric Wire Corporation, Lisborn, N.H.

In order to most effectively decelerate the electrons striking the anode, a heavy metal material can be used for the anode 24, such as tungsten or gold. The material used for the cathode base 26 depends on how the diamond film is formed. The thin diamond film 28 can be obtained by chemical vapor deposition, as is known in the art. Various materials may serve as an effective substrate for diamond film synthesis by chemical vapor deposition, such as tungsten, molybdenum, and tantalum. As described more fully below, the diamond film could also be fabricated by other methods, such as by laser ion deposition, making a wider range of materials available for the base of the cathode.

The term diamond film, as used herein, contemplates a coating of carbon having diamond-like bonds which demonstrate negative electron affinity. It is also desirable to have sufficient conductivity to create a constant supply of electrons to the surface of the cathode. The presence of some graphite bonds in the diamond film will contribute to conductivity. Thus a combination of a diamond film having both sp3 carbon bonds, to function as a cathode, and some sp2 carbon bonds, to facilitate conductivity, is particularly suited for use in such a system. Other elements may also be present in the film in small quantities. According to the invention, the diamond film will have the property that it can emit electrons at electrical fields greater than or equal to about 20 keV/micron. This required electric field is extremely low when compared to that required for metal emitters such as molybdenum or silicon, which require greater than 1,000 keV/micron.

A getter 30 is disposed within the vacuum housing 23 in order to aid in creating and maintaining a vacuum condition of high quality. The getter 30 has an activation temperature, at which it will react with stray gas molecules in the vacuum. After the getter 30 is disposed within the vacuum housing and the housing pumped out, the device is heated to the activation temperature. It is desirable that the getter used have an activation temperature that is not so high that the x-ray device will be damaged when heated to the activation temperature. A SAES ST 101 alloy getter could be used, which has an activation temperature in the range 750 to 900° C. and is composed of approximately 64% zirconium and 16% aluminum. A ST 707 alloy getter could also be used, which has an activation temperature in the range 400–500° C. and is composed of approximately 70% zirconium, 24.6% vanadium, and 5.4% iron.

A wall of the vacuum chamber 36 should be transparent to x-rays in order to allow the full dosage to reach the lumen wall. The wall 36 can comprise boron nitride, such as pyrolytic boron nitride or another metal or ceramic material which is transparent to x-rays. Other possibilities include isotropic boron nitride, anisotropic boron nitride, beryllium, beryllium oxide, aluminum, aluminum oxide, or graphite.

In the x-ray device an electrical field exists at the surface of the cathode 26 and current flows from the cathode 26 to the anode 24, while just on the outside of the vacuum housing a conductive braid or solder 44 is held at ground. In accordance with the present invention, these two potentials must be insulated from each other or electrical flashover will occur. A vacuum wall of pyrolytic boron nitride can provide some insulation. If a metal is used as the vacuum chamber wall 36, an insulative layer is necessary. As additional protection against electrical flashover, an electrically insulating material 50 can be placed at the joints of the vacuum chamber wall. The vacuum chamber further includes a biocompatible coating 46, such as polyethylene, polyurethane or Teflon®. The joints 34 between the vacuum chamber wall 36 and the anode 24 can be vacuum furnace brazed.

When used to radiate the wall of a lumen, according to one embodiment of the invention, the x-ray device is placed within a catheter. The catheter is introduced into the lumen to be treated through the skin. The x-ray device is then guided through the lumen, using techniques known in the art, until it is positioned near the area to be radiated.

The high voltage generator is activated and an electrical field is established across the cathode 28 and the anode 24. A voltage of 10 kilovolts or even higher may be applied to the transmissive device 20 of the present invention without causing electrical flashover. Further, voltages of 20 kilovolts or 30 kilovolts may be applied without electrical flashover. The thin diamond coating 28 loses electrons which are accelerated toward the anode 24. As the electrons are decelerated by the anode 24, electromagnetic radiation is emitted by the material of the anode 24. In this manner, x-ray radiation is produced by the Bremsstrahlung effect. As the x-ray radiation impinges upon the wall of the lumen, it inhibits smooth muscle proliferation. Thus, the x-ray catheter device can be used to effectively prevent restenosis. When the desired dosage has been delivered, the voltage source is discontinued and the catheter withdrawn from the body.

A certain amount of heat is generally generated by the x-ray unit at the anode. Thus, some mechanism for cooling the structure may be required. When used in an artery, the typical blood flow to an artery is about 50–60 $cm^3$/minute, which aids in dissipating heat conducted through the vacuum housing. Where the x-ray device is used in other body systems, additional cooling methods may be required.

Figure 2:
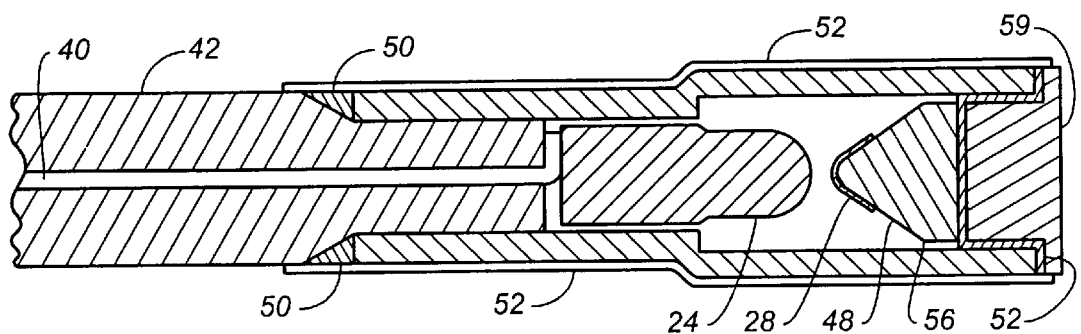
FIG. 2 shows an exploded cross-sectional view of another embodiment of the x-ray device of the present invention.

Now referring to FIG. 2, another embodiment of the x-ray device of the present invention is illustrated. In the embodiment of FIG. 2, a thin diamond film is placed directly on a getter. According to the invention, by incorporating the getter into the cathode structure, significant size advantages can be obtained.

Treatments for cardiovascular disease continue to become less invasive in the patient's body and therefore less stressful to the patient's system. Size improvements on an x-ray device could reduce the size of the required incision, improve maneuverability, decrease the stress on the lumen, and enable the device to reach more remote locations in the patient's body. By combining a cathode and a getter in an x-ray device, it is possible to eliminate components and permit a significant size reduction.

Laser ion source deposition may be used to place the diamond film directly upon a getter. A traditional chemical vapor deposition process takes place at approximately 900° C. Therefore, a getter used as a substrate in such a process would be activated and used up during the deposition process. However, the use of a laser ion source deposition process, which can be carried out at room temperature, allows a diamond film to be created on a getter without activating the getter. A laser ion source deposition process is described in U.S. Pat. No. 4,987,007, Wagal et al. U.S. Pat. No. 4,987,007, in its entirety is hereby incorporated by reference. The outer diameter of the integrated x-ray device of the embodiment illustrated in FIG. 2 will be less than or equal to approximately one and one quarter millimeters.

The outer vacuum housing features of FIG. 1 may also be used in the embodiment shown in FIG. 2, although these features are not illustrated in FIG. 2. For example, the outer biocompatible layer, vacuum furnace brazed joints and insulating material may be used in the embodiment of FIG. 2. In FIG. 2, a conductive solder material 52 provides an electrical connection between the external conductive layer 42 of the coaxial cable and the cathode base 48.

The getter 56 will be conductive enough to provide the electrical connection between the thin diamond film 28 and the conductive solder 52. The ST 707 alloy getter could also be used, which has an activation temperature in the range 400–500° C. and is composed of approximately 70% zirconium, 24.6% vanadium, and 5.4% iron.

Figure 3:
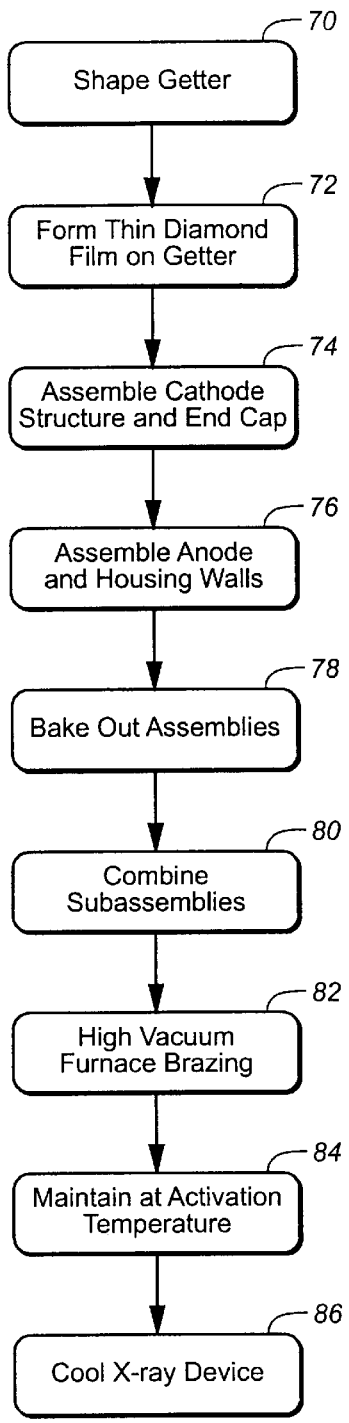
FIG. 3 illustrates the steps involved in a method of fabricating an x-ray device of the present invention.

FIG. 3 shows a method for creating the x-ray device of the second embodiment. First, the getter is machined into a desirable shape for the cathode in step 70. A cone shape or rounded cone shape, for example, may be used for the shape of the cathode. Next, a thin diamond film is formed on a tip portion of the getter in step 72. The tip portion of the getter corresponds to a cathode structure. The diamond film formation is carried out at a temperature below the activation temperature of the getter using, for example, laser ion source deposition techniques. Two subassemblies are constructed. In step 74, one subassembly comprises the cathode structure and an end cap 59. The other subassembly of step 76 comprises the anode 24 and the vacuum chamber walls 36. These two subassemblies are sealed in a high vacuum furnace and heated to approximately 400–500° C. to bake out gas molecules from the materials for about two hours in step 78. The subassemblies are sealed together in step 80, while still at high vacuum furnace conditions. The temperature is increased to approximately 500–700° C. for step 82 high vacuum furnace brazing of the joints of the x-ray device. The device is maintained at a high temperature for several hours to thoroughly activate the getter in step 84. The device is cooled in step 86, tested, and cables are attached.

In the device of this method, the getter is a miniature vacuum pump disposed within the vacuum housing. This method permits the manufacture of an x-ray device having an outer diameter of less than or equal to approximately one and one-quarter millimeter.

The various embodiments described above are provided by way of illustration only and should not be construed to limit the invention. Those skilled in the art will readily recognize various modifications and changes which may be made to the present invention without strictly following the exemplary embodiments and applications illustrated and described herein, and without departing from the true spirit and scope of the present invention which is set forth in the following claims.

We claim:

1. A device for delivering localized x-ray radiation in a patient's vascular system, the device comprising:

a shaft, including a proximal and a distal portion;

a vacuum housing coupled to the distal portion of the shaft, the vacuum housing having an outside, the vacuum housing having an outer diameter less than or equal to approximately two and one-half millimeter;

an anode disposed within the vacuum housing;

a cathode structure disposed within the vacuum housing, the cathode structure including a thin diamond film, the thin diamond film being operative with the anode to produce the localized x-ray radiation, and a first electrical field associated with the cathode and anode;

a conductive layer on the vacuum housing outside, the conductive layer being electrically connected to the cathode, and a second electrical field associated with the conductive layer; and an insulator for insulating the first electrical field from the second electrical field.

2. The device of claim 1 further comprising a voltage source coupled to the proximal portion of the shaft and operative with the anode and cathode structure to produce the localized x-ray radiation.

3. The device of claim 1 further comprising a getter disposed within the vacuum housing.

4. The device of claim 1 wherein the cathode structure further comprises a getter on which the thin diamond film is disposed.

5. The device of claim 4 wherein the getter is sufficiently conductive to facilitate the application of an electric potential to the thin diamond film.

6. The device of claim 4 wherein the getter is comprised of approximately 70% zirconium, 24.6% vanadium, and 5.4% iron.

7. The device of claim 1 wherein the anode is comprised of tungsten.

8. The device of claim 1 wherein the cathode structure is comprised of a molybdenum base on which the thin diamond film is disposed.

9. The device of claim 1 wherein the cathode structure is comprised of a silicon base on which the thin diamond film is disposed.

10. The device of claim 1 wherein the cathode structure is comprised of a tantalum base on which the thin diamond film is disposed.

11. The device of claim 1 wherein an outer diameter of the vacuum housing is less than or equal to one and one-quarter millimeters.

12. The device of claim 1 further comprising a coaxial conductor having a proximal and distal portion, the coaxial conductor coupled to the anode and the cathode, the coaxial conductor disposed within the shaft and coupled to the voltage source.

13. The device of claim 1 wherein the shaft is a catheter and the vacuum housing is disposed within the catheter.

* * * * *